United States Patent [19]

Itoh

[11] Patent Number: 4,839,528
[45] Date of Patent: Jun. 13, 1989

[54] PARTICLE ANALYZING APPARATUS USING AN AFOCAL LIGHT BEAM

[75] Inventor: Yuji Itoh, Chigasaki, Japan

[73] Assignee: Canon Kabushiki Kaisha, Tokyo, Japan

[21] Appl. No.: 49,522

[22] Filed: May 14, 1987

[30] Foreign Application Priority Data

May 17, 1986 [JP] Japan .................. 61-112987
Mar. 30, 1987 [JP] Japan .................. 62-078211

[51] Int. Cl.$^4$ .................. G01N 15/00; G01N 21/51
[52] U.S. Cl. .................. 250/574; 250/576; 356/338
[58] Field of Search .................. 356/335–336, 356/338–341, 343, 410–411, 246; 250/573–576, 222.2

[56] References Cited

U.S. PATENT DOCUMENTS 4,072,421  2/1978  Coyne et al. .................. 356/338
4,179,218  12/1979  Erdmann et al. .................. 250/574
4,251,733  2/1981  Hirleman, Jr. .................. 356/335

Primary Examiner—Edward P. Westin
Attorney, Agent, or Firm—Fitzpatrick, Cella, Harper & Scinto

[57] ABSTRACT

A light is applied to particles to be examined in a cell, the scattered light from the particles to be examined is converted to an afocal light, a beam splitter is provided in the afocal light beam, and photometering and observation of the cell are efficiently effected in two optical paths branched off by the beam splitter.

7 Claims, 2 Drawing Sheets

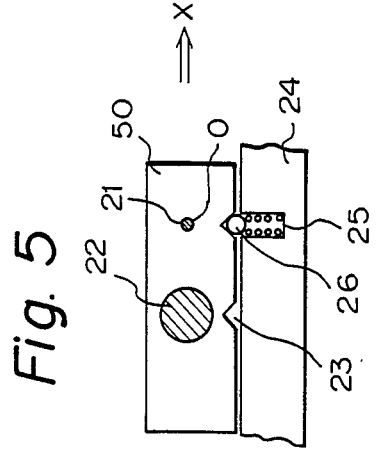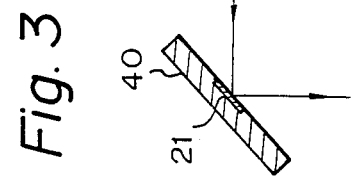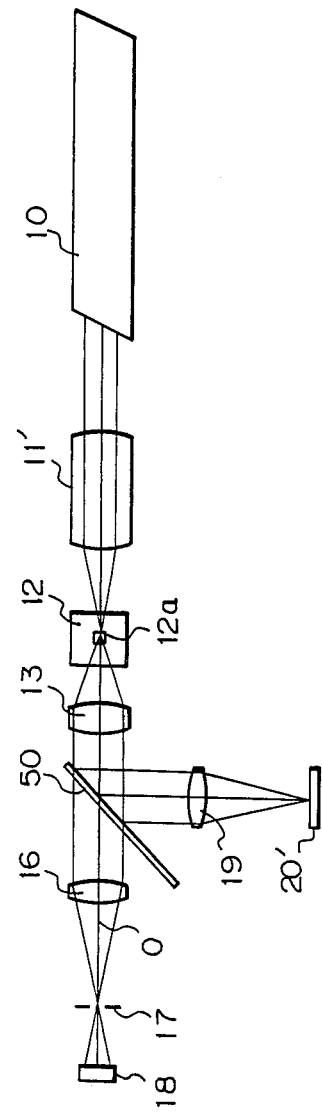

PARTICLE ANALYZING APPARATUS USING AN AFOCAL LIGHT BEAM

BACKGROUND OF THE INVENTION

1. Field of the Invention

This invention relates to a particle analyzing apparatus which effects beam splitting of the observation optical system and photometering optical system of a cell such as a flow cell containing particles to be examined and irradiated by an irradiating beam.

2. Related Background Art

In a prior-art particle analyzing apparatus used in a flow sightmeter, an irradiating light is applied to particles to be examined wrapped in sheath liquid and passing through a circulating portion having a minute cross-section, for example, of 200 $\mu$m $\times$ 200 $\mu$m in the central portion of the flow cell, and by the resultant forward and sideways scattered light, it is possible to obtain the particulate properties such as the shape, size and refractive index of the particles to be examined. The flow sightmeter is known from U.S. Pat. Nos. 4,643,566; 4,690,561; 4,715,708 and 4,732,479, and U.S. application Ser. Nos. 106,025 and 219,816.

In the case of an example of the prior art shown in FIG. 1(A) of the accompanying drawings, the forward scattered light of particles to be examined flowing through the circulating portion 1a of a flow cell 1 by a laser light enters a photodetector 5 via a beam splitter 2 having cemented surfaces, an objective 3 and an aperture 4. A stopper 6 disposed in front of the objective 3 functions to cut the laser light (0-order light) which directly enters the photodetecter 5. In a beam observing optical system bent at 90° by the beam splitter 2, an image for monitoring the beam shape and position of the irradiating laser light or detecting the stain or the like of the interior of the flow cell 1 is formed on an image sensor 8 through an imaging lens 7.

In this case, the stopper 6 is disposed rearwardly of the beam splitter 2 in order to detect the beam shape of the laser light. Thus, the direct laser light (0-order light) enters the cemented surfaces of the beam splitter 2, whereby an optical variation occurs in the adhesive agent of the cemented portion. In the interest of reducing aberrations, it is not preferable to dispose a planar beam splitter 2 having no cemented surfaces in a diverging light beam system ahead of the objective 3 because the light beam will be reflected by the front and rear surfaces of the beam splitter and the image formed by the imaging lens 7 will be a dual image.

FIG. 1(B) of the accompanying drawings, shows another example of the prior art. A planar beam splitter 2' having no cemented surfaces is disposed rearwardly of an objective 3', whereby a light beam travelling sideways is imaged on a screen 9 by a lens 7' to thereby enable the circulating portion 1a of the flow cell to be observed.

In this case, the light is intercepted by the presence of a stopper 6 disposed forwardly of the beam splitter 2' and the resolving power is reduced when the circulating portion is observed. Also, because the beam splitter 2' is disposed in the diverging light beam system, the light is reflected by the front and rear surfaces of the beam splitter 2' and the image formed by the imaging lens 7' becomes a dual image.

SUMMARY OF THE INVENTION

It is an object of the present invention to eliminate the above-noted disadvantage peculiar to the prior art and to provide a particle analyzing apparatus of good accuracy which is free from the optical influence of a beam splitter.

It is a further object of the present invention to provide a particle analyzing apparatus in which light in not intercepted during the observation of the circulating portion of a flow cell to thereby prevent the resolving power from being reduced.

It is still a further object of the present invention to provide a particle analyzing apparatus in which any irregularity of the quantity of light in the observation field by the difference in the reflecting power of a beam splitter is not caused during the observation of the circulating portion of the flow cell.

BRIEF DESCRIPTION OF THE DRAWINGS

FIG. 3 illustrates the essential portion of a second embodiment of the present invention.

FIGS. 4 and 5 illustrate the entire construction and the essential portions, respectively, of a third embodiment of the present invention.

DESCRIPTION OF THE PREFERRED EMBODIMENTS

Figure 1A:
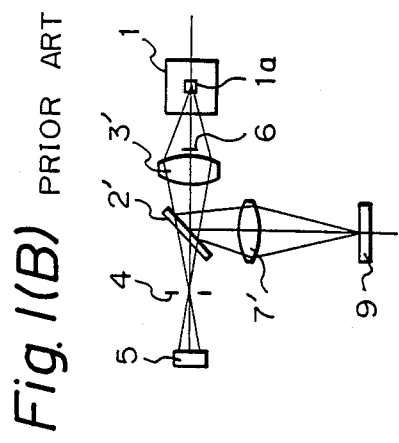
FIGS. 1(A) and 1(B) show different examples of the prior art.
Figure 1B:
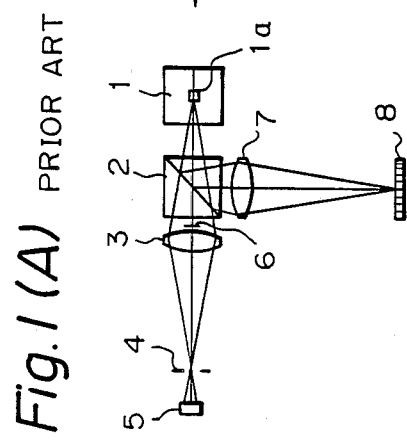
Figure 2:
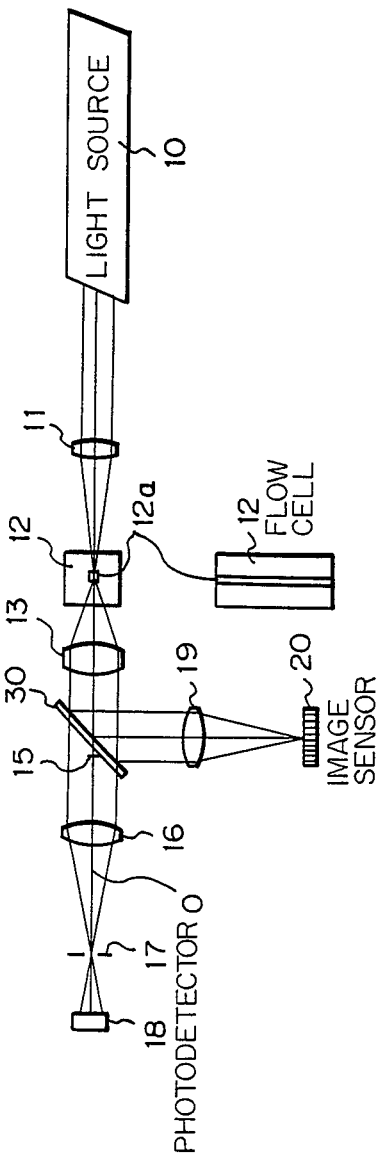
FIG. 2 shows the entire construction of a first embodiment of the present invention.

Referring to FIG. 2, reference numeral 10 designates a laser light source, and along the optic axis thereof, there are arranged in succession an imaging lens 11, a flow cell 12, an objective 13, a beam splitter 30, a stopper 15, an imaging lens 16, an aperture 17 and a photodetector 18. Also, an imaging lens 19 and an image sensor 20 are disposed on the reflection side of the beam splitter 30. The portion between the objective 13 and the imaging lens 16 is an afocal optical system.

The laser light from the laser light source 10 is condensed near the center of the portion 12a of the flow cell 12 by the imaging lens 11. The forward scattered light by particles to be examined enters the photodetector 18 via the beam splitter 30, the imaging lens 16 and the aperture 17. In the optical path bent at 90° by the beam splitter 30 comprising a half-mirror or the like, an image is formed on the image sensor 20 by the imaging lens 19 to monitor the shape of the irradiating beam in the flow cell 12. Since the portion between the objective 13 and the imaging lens 16 is an afocal optical system, the image reflected by the front and rear surfaces of the beam splitter 30 and formed by the imaging lens 19 does not become a dual image. This also holds true of the forward scattered light photometering optical system, and there is no problem with respect to aberrations.

Also, since the stopper 15 being disposed rearwardly of the beam splitter 30, the direct light from the laser light source to the photodetector 18 can be cut. The light travelling to the image sensor 20 is not intercepted by the stopper.

FIG. 3 illustrates the essential portion of a second embodiment of the present invention, and shows a beam splitter 40 inserted in place of the beam splitter 30 of FIG. 2. The portion corresponding to a reflecting mirror of total reflection property provided on the cell reflecting surface of the beam splitter 40 acts as a stopper for the forward scattered light photometering optical system and directs the laser light to the image sensor without intercepting it.

FIGS. 4 and 5 show a third embodiment of the present invention. In this embodiment, a total reflection mirror for observation of the cell is provided and any irregularity based on the difference in reflecting power does not occur in the observation field during the observation of the cell. In FIG. 4, reference numerals similar to those in FIG. 2 designate similar members. Reference numeral 11' designates an imaging lens, reference numeral 20' denotes a screen, and reference numeral 50 designates a beam splitter.

In FIG. 4, the imaging lens 19 and the screen 20' (or the ceiling or the like) are disposed on the reflection side of the beam splitter 50. The portion between the objective 13 and the imaging lens 16 is an afocal optical system. FIG. 5 is a view of the beam splitter 50 as seen from the direction of the optic axis 0. On the reflecting surface of the beam splitter 50 which is adjacent to the cell, there is provided, in addition to the total reflection mirror 21 shown in FIG. 3, a total reflection mirror 22 for observation which is larger than the total reflection mirror 21 so as to project the light onto the screen 20' and which is for observing the circulating portion of the flow cell. The reflection power of the beam splitter 50 outside the areas of the total reflection mirrors 21 and 22 is, e.g., 50%. The beam splitter 50 has two positioning cut-aways 23 so that the total reflection mirrors 21 and 22 on the beam splitter 50 can be positioned on the optic axis 0 by a spring 25 and a steel ball 26 provided on a base plate 24 when the beam splitter 50 is moved perpendicularly to the optic axis.

When the beam splitter 50 is set at its position as shown in FIG. 5, the center of the total reflection mirror 21 coincides with the optic axis 0 and acts as a stopper which eliminates the direct light (0-order light) of the laser. The laser light from the laser light source 10 is condensed near the central portion of the flow path in the portion 12a of the flow cell 12 by the imaging lens 11', and the forward scattered light there is photometered by the photodetector 18 via the objective 13, the beam splitter 50, the imaging lens 16 and the aperture 17.

When the beam splitter 50 is then slid in the direction of arrow X in FIG. 5 and the cut-away 23 is moved to the position of the steel ball 26, the center of the total reflection mirror 22 coincides with the optic axis 0 and therefore, the laser light is reflected by the total reflection mirror 22 and the circulating portion 12a of the flow cell 12 is projected onto the screen 20'. Thus, on the basis of the edge portion of the portion 12a of the flow cell 12, the aligned state and the stain of the inner surface of the flow cell can be observed with no irregularity being caused by the difference in the reflecting power of the beam splitter.

In the above-described embodiments, design is made such that the stopper and the total reflection mirror for observing the circulating portion of the flow cell are changed over by sliding the beam splitter 50 in a plane perpendicular to the optic axis, but a similar effect may also be obtained by providing a similar total reflection mirror on a disk-like beam splitter and rotating and changing over it in a plane perpendicular to the optic axis by a rotating mechanism. In the embodiment of FIG. 5, the stopper portion is made reflective, but alternatively, it may be made absorbent.

I claim:

1. A particle analyzing apparatus comprising:
    an irradiating system for applying a light to particles to be examined in a cell;
    means for converting the scattered light from the particles to be examined to an afocal light beam;
    a beam splitter provided in the afocal light beam;
    a photometering system provided in a first optical path branched off by said beam splitter for photometering the scattered light from the particles to be examined;
    an observation system provided in a second optical path branched off by said beam splitter for observing the cell;
    a stopper for eliminating a direct light from said irradiating system and preventing direct light from reaching said photometering system is provided on a reflecting surface of said beam splitter, said stopper being provided on the optical axis of said beam splitter; and
    a total reflection area for observing the cell, said total reflection area being provided discretely from said stopper, with said total reflection area being on said beam splitter and being larger than said stopper.

2. A particle analyzing apparatus according to claim 1, wherein said stopper and said total reflection area for observing the cell are provided on the reflecting surface of said beam splitter which is adjacent to the cell.

3. A particle analyzing apparatus according to claim 2, wherein said beam splitter is movable perpendicularly along the optical axis.

4. A particle analyzing apparatus according to claim 3, wherein said stopper is provided as a reflective stopper.

5. A particle analyzing apparatus according to claim 3, wherein said stopper is provided as an absorbing stopper.

6. A particle analyzing apparatus according to claim 1, wherein said beam splitter is provided in the optical path of the forward scattered light.

7. A particle analyzing apparatus according to claim 6, wherein said irradiating system applies a laser light, and the particles to be examined flow through said cell in a direction perpendicular to the irradiation optic axis.

* * * * *